United States Patent
Huard et al.

(10) Patent No.: US 6,517,848 B1
(45) Date of Patent: *Feb. 11, 2003

(54) METHOD FOR SEQUESTRATION OF SKIN IRRITANTS WITH ABSORBENT ARTICLE COMPOSITION

(75) Inventors: Linda Susan Huard, Appleton, WI (US); David John Tyrrell, Appleton, WI (US); David Roland Otts, Appleton, WI (US); Bernard Joseph Minerath, III, Oshkosh, WI (US); Brenda Marie Nelson, Appleton, WI (US); Chantel Spring Buhrow, Weyauwega, WI (US); Dennis Stein Everhart, Alpharetta, GA (US); Robert Cosmo DiLuccio, Alpharetta, GA (US); Frank Jerrel Akin, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/475,825

(22) Filed: Dec. 30, 1999

Related U.S. Application Data

(60) Provisional application No. 60/114,497, filed on Dec. 31, 1998, and provisional application No. 60/114,496, filed on Dec. 31, 1998.

(51) Int. Cl.[7] .................. A01N 25/34; A61K 6/00; A61K 9/00; A61F 13/00
(52) U.S. Cl. .............. 424/402; 424/401; 424/400; 424/78.08; 424/443; 424/604; 424/367; 424/368
(58) Field of Search .................. 604/367, 368; 424/402, 78.08

(56) References Cited

U.S. PATENT DOCUMENTS

| 144,315 A | 11/1873 | Cooper |
|---|---|---|
| 433,827 A | 8/1890 | Schultz |
| 795,562 A | 7/1905 | Tatti |

(List continued on next page.)

FOREIGN PATENT DOCUMENTS

| DE | 2 260 612 | 9/1974 | .......... A47K/10/16 |
|---|---|---|---|
| DE | 3 924 898 | 1/1991 | .......... D21H/17/71 |
| EP | 0 191 128 | * 4/1985 | |

(List continued on next page.)

OTHER PUBLICATIONS

Sato, J. et al., *Cholesterol Sulfate Inhibits Proteases that are Involved in Desquamation of Stratum Corneum*, The Journal of Investigative Dermatology, pp. 189–193 (1998).

(List continued on next page.)

Primary Examiner—Thurman K. Page
Assistant Examiner—Isis Ghali
(74) Attorney, Agent, or Firm—Pauley Peterson Kinne & Erickson

(57) ABSTRACT

Methods of using absorbent personal care articles, such a diapers and adult incontinent briefs, comprising an absorbent article and having disposed thereon a skin irritant sequestering effective amount of an unmodified particulate skin irritant sequestering agent, and a lipophilic skin health benefit agent are provided. An unmodified particulate skin irritant sequestering agent can be a clay, such as bentonite or laponite unmodified by organic amphiphilic compounds. A lipophilic skin health benefit agent can be stearic acid, isoparrafin, petrolatum, and a combination thereof. The skin irritant can be bound to the sequestering agent either on an individual's skin or on the absorbent article.

14 Claims, 7 Drawing Sheets

U.S. PATENT DOCUMENTS

| | | | |
|---|---|---|---|
| 810,115 A | 1/1906 | Green | |
| 1,098,176 A | 5/1914 | Schwerin | |
| 1,634,974 A | 7/1927 | Bucci | |
| 1,900,973 A | 3/1933 | Bertsch | |
| 1,999,161 A | 4/1935 | Walton | 167/91 |
| 2,020,517 A | 11/1935 | Rewald | 8/6 |
| 2,137,310 A | 11/1938 | Sommer | 92/21 |
| 2,186,709 A | 1/1940 | Rowland | 92/21 |
| 2,317,908 A | 4/1943 | Grady | 167/14 |
| 2,523,316 A | 9/1950 | McClenahan et al. | 167/63 |
| 2,678,320 A | 5/1954 | Scharf | 252/354 |
| 2,684,321 A | 7/1954 | Thurmon et al. | 167/58 |
| 2,795,568 A | 6/1957 | Ruehrwein | 260/41 |
| 2,883,356 A | 4/1959 | Gluesenkamp | 260/37 |
| 2,944,931 A | 7/1960 | Yang | 162/179 |
| 2,999,265 A | 9/1961 | Duane et al. | 15/506 |
| 3,069,361 A | 12/1962 | Cogswell | 252/363.5 |
| 3,208,984 A | 9/1965 | Dekking | 260/89.5 |
| 3,243,369 A | 3/1966 | Dekking | 252/28 |
| 3,264,188 A | 8/1966 | Gresham | 167/84 |
| 3,296,055 A | 1/1967 | Wilkins | 156/433 |
| 3,431,133 A | 3/1969 | Braude et al. | 117/24 |
| 3,594,221 A | 7/1971 | Baldwin | 117/138.5 |
| 3,619,280 A | 11/1971 | Scheuer | 117/154 |
| 3,935,363 A | 1/1976 | Burkholder et al. | 428/281 |
| 4,100,324 A | 7/1978 | Anderson et al. | 428/288 |
| 4,273,786 A * | 6/1981 | Kraskin | |
| 4,381,782 A | 5/1983 | Mazurak et al. | 604/368 |
| 4,450,151 A | 5/1984 | Shinozawa | 424/46 |
| 4,463,017 A | 7/1984 | Hidalgo et al. | 424/359 |
| 4,556,560 A | 12/1985 | Buckingham | 424/145 |
| 4,559,157 A | 12/1985 | Smith et al. | 252/90 |
| 4,657,537 A | 4/1987 | Zimmerer | 604/360 |
| 4,685,909 A | 8/1987 | Berg et al. | 604/360 |
| 4,704,116 A | 11/1987 | Enloe | 604/385 A |
| 4,707,293 A | 11/1987 | Ferro | 252/174.17 |
| 4,798,603 A | 1/1989 | Meyer et al. | 604/378 |
| 4,818,464 A | 4/1989 | Lau | 264/510 |
| 4,846,823 A | 7/1989 | Enloe | 604/385.2 |
| 4,857,308 A | 8/1989 | Fukasawa et al. | 424/63 |
| 4,943,350 A | 7/1990 | Bogart et al. | 162/158 |
| 5,017,361 A | 5/1991 | Powell, Jr. et al. | 424/46 |
| 5,019,073 A | 5/1991 | Roessler et al. | 604/391 |
| 5,091,193 A * | 2/1992 | Enjolras et al. | |
| 5,109,533 A | 4/1992 | Mine et al. | 455/63 |
| 5,122,418 A | 6/1992 | Nakane et al. | 424/401 |
| 5,176,671 A | 1/1993 | Roessler et al. | 604/391 |
| 5,190,533 A | 3/1993 | Blackburn | 604/367 |
| 5,192,606 A | 3/1993 | Proxmire et al. | 428/284 |
| 5,288,546 A | 2/1994 | Roessler et al. | 428/284 |
| 5,304,162 A | 4/1994 | Kuen | 604/391 |
| 5,306,444 A | 4/1994 | Kitamura et al. | 252/546 |
| 5,318,555 A | 6/1994 | Siebers et al. | 604/390 |
| 5,364,382 A | 11/1994 | Latimer et al. | 604/378 |
| 5,374,262 A | 12/1994 | Keuhn, Jr. et al. | 604/391 |
| 5,386,595 A | 2/1995 | Kuen et al. | 2/400 |
| 5,399,219 A | 3/1995 | Roessler et al. | 156/259 |
| 5,403,302 A | 4/1995 | Roessler et al. | 604/391 |
| 5,405,342 A | 4/1995 | Roessler et al. | 604/364 |
| 5,413,570 A | 5/1995 | Enloe | 604/385.2 |
| 5,415,644 A | 5/1995 | Enloe | 604/385.2 |
| 5,423,789 A | 6/1995 | Kuen | 604/386 |
| 5,429,629 A | 7/1995 | Latimer et al. | 604/378 |
| 5,434,183 A | 7/1995 | Larsson-Blackström | 514/549 |
| 5,486,166 A | 1/1996 | Bishop et al. | 604/366 |
| 5,490,846 A | 2/1996 | Ellis et al. | 604/366 |
| 5,508,034 A | 4/1996 | Bernstein | 424/401 |
| 5,509,915 A | 4/1996 | Hanson et al. | 604/378 |
| 5,599,338 A | 2/1997 | Enloe | 604/385.2 |
| 5,611,890 A | 3/1997 | Vinson et al. | 162/111 |
| 5,612,307 A | 3/1997 | Chambers et al. | 510/406 |
| 5,631,012 A | 5/1997 | Shanni | 424/401 |
| 5,641,483 A | 6/1997 | Beaulieu | 424/78.06 |
| 5,643,899 A | 7/1997 | Elias et al. | 514/171 |
| 5,651,862 A | 7/1997 | Anderson et al. | 162/127 |
| 5,658,559 A | 8/1997 | Smith | 424/78.02 |
| 5,702,709 A | 12/1997 | Schulz et al. | 424/401 |
| 5,714,154 A | 2/1998 | Le Hen-Ferrenbach et al. | 424/401 |
| 5,720,966 A | 2/1998 | Ostendorf | 424/402 |
| 5,738,856 A | 4/1998 | Korb et al. | 424/401 |
| 5,738,859 A | 4/1998 | Posner | 424/401 |
| 5,869,033 A | 2/1999 | Schulz | 424/78.02 |
| 5,908,836 A | 6/1999 | Bar-Shalom et al. | 514/53 |
| 5,945,409 A | 8/1999 | Crandall | 514/78 |
| 5,951,991 A | 9/1999 | Wagner et al. | 424/401 |
| 5,958,185 A | 9/1999 | Vinson et al. | 162/111 |
| 5,972,359 A | 10/1999 | Sine et al. | 424/401 |
| 5,998,695 A * | 12/1999 | Roe et al. | 604/367 |
| 6,001,377 A | 12/1999 | SaNogueira, Jr. et al. | 424/401 |
| 6,015,574 A | 1/2000 | Cannell et al. | 424/450 |
| 6,049,915 A | 4/2000 | Malowaniec | 2/400 |
| 6,051,749 A * | 4/2000 | Schultz | 604/368 |
| 6,066,673 A | 5/2000 | Mellver et al. | 514/634 |
| 6,107,537 A * | 8/2000 | Elder et al. | |
| 6,120,488 A * | 9/2000 | VanRijswijck et al. | |

FOREIGN PATENT DOCUMENTS

| | | | | |
|---|---|---|---|---|
| EP | 365 726 | 5/1990 | | D21H/21/14 |
| GB | 1 327 041 | 8/1973 | | D21J/7/00 |
| JP | 1-221575 | 9/1959 | | D06M/15/263 |
| JP | 4011-313 | 6/1977 | | |
| JP | 8220-896 | 6/1982 | | |
| JP | 62-250038 | 10/1987 | | C08J/9/00 |
| JP | 62-254841 | 11/1987 | | |
| JP | 63-192703 | 8/1988 | | A61K/7/48 |
| JP | 3008-897 | 8/1989 | | |
| JP | 2-057252 | 2/1990 | | A61F/13/15 |
| JP | 2-200607 | 8/1990 | | A61K/7/00 |
| JP | 2-264078 | 10/1990 | | A61F/5/44 |
| JP | 4-082824 | 3/1992 | | A61K/7/00 |
| JP | 4-272296 | 9/1992 | | |
| JP | 4-273809 | 9/1992 | | |
| JP | 6-080547 | 3/1994 | | A61K/7/48 |
| JP | 6-345633 | 12/1994 | | A61K/7/48 |
| JP | 7-069827 | 3/1995 | | A61K/7/00 |
| JP | 7-316444 | 12/1995 | | C08L/101/14 |
| JP | 8-047509 | 2/1996 | | A61F/13/54 |
| JP | 8-119846 | 5/1996 | | A61K/7/48 |
| JP | 9-136836 | 5/1997 | | A61K/31/215 |
| JP | 9-302138 | 11/1997 | | C08K/3/22 |
| JP | 10-175843 | 6/1998 | | |
| SU | 1781355 | 4/1990 | | |
| WO | 97/17494 | 5/1997 | | D21H/27/40 |
| WO | 97/31153 | 8/1997 | | D21H/21/24 |
| WO | 97/38735 | 10/1997 | | A61L/15/18 |
| WO | 98/13549 | 4/1998 | | D21H/25/00 |
| WO | 98/17856 | 4/1998 | | D21C/9/00 |
| WO | 98/28491 | 7/1998 | | D21H/17/67 |
| WO | 98/34589 | 8/1998 | | A61K/7/48 |
| WO | 99/26610 | 6/1999 | | A61K/31/00 |
| WO | 99/45974 | 9/1999 | | A61L/15/44 |
| WO | 99/46316 | 9/1999 | | C08G/65/48 |

OTHER PUBLICATIONS

Adachi, M. et al., *Selective Separation of Trypsin from Pancreatin Using Bioaffinity in Reverse Micellar System Composed of a Nonionic Surfactant*, Biotechnology and Bioengineering, vol. 58, No. 6 (1998).

Kadam, K., *Reverse Micelles as a Bioseparation Tool*, Enzyme and Microbial Technology, vol. 8, pp. 266–273 (1986).

* cited by examiner

METHOD FOR SEQUESTRATION OF SKIN IRRITANTS WITH ABSORBENT ARTICLE COMPOSITION

CROSS-RELATION TO PRIOR APPLICATIONS

The present application claims priority to U.S. Provisional Application Nos. 60/114,497 and 60/114,496 both filed on Dec. 31, 1998.

BACKGROUND OF THE INVENTION

The stratum corneum is the outer-most layer of the skin that provides a barrier against internal water loss and the absorption of potentially hazardous materials from the environment. Its structure has been compared to a "brick and mortar" system where skin cells (bricks) are imbedded in a complex mixture of lipids (mortar). Disruption of either of these two components can lead to the impairment of skin barrier function.

Enzymes commonly found in biological fluids, particularly proteases and lipases, are known to damage skin barrier function and cause skin inflammation. For example, prolonged exposure of the skin to fecal proteases and lipases is thought to be a major cause of skin damage that leads to diaper dermatitis in infants. The care of skin in individuals with ostomies is difficult due to the frequent contact of digestive enzymes with skin surrounding the ostomy. These enzymes can degrade skin proteins and lipids and cause irritation of the skin.

Compositions and/or materials or articles that reduce the action of these enzymes on skin will allow for enhanced skin health and the prevention of inflammatory skin diseases such as diaper dermatitis.

There are several approaches known in the art for inhibiting the action of fecal enzymes on skin. WO 99/45974 discloses the use of protease inhibitors in absorbent articles in preventing diaper dermatitis. Inhibitors are defined in this reference as any substance that inhibits the activity of proteases in seven in vitro assays against defined substrates. These inhibitors are required to meet at least one of seven criteria for $IC_{50}$ (the concentration that inhibits 50% of the enzyme activity) and to reversibly or irreversibly inhibit the hydrolytic action of one or more proteases. WO 99/26610 discloses the use of lipase inhibitors in absorbent articles in preventing diaper dermatitis. These above-mentioned approaches to inhibiting the action of digestive enzymes on skin are limited in that diffusion of the inhibitors into the skin may cause adverse effects by inhibiting endogenous enzymes that are important to normal skin function. For example, it is known that topical application of cholesterol sulfate, a potent serine protease inhibitor, inhibits skin proteases that are responsible for normal desquamation (J. Invest. Dermatol. 111:189–193, 1998). Abnormally dry, or xerotic, skin may arise from topical treatment with protease inhibitors that are able to diffuse into the skin. Thus, what are needed are substances that do not penetrate the surface of the skin and prevent the degradative action of exogenous enzymes, such as fecal enzymes, on proteins within the skin. WO 99/46316 discloses the creation of polymeric inhibitors to inhibit fecal protease-mediated skin irritation. These polymers purportedly do not penetrate the skin surface but still exert their action by directly inhibiting the activity of the enzymes against other substrates.

Compositions that adsorb and inactivate fecal enzymes and thereby prevent them from penetrating into the skin have been disclosed. PCT publication WO 97/38735 and U.S. Pat. No. 5,869,033 teach the use of organophilic clays, such as activated quarternium-18 bentonite, to absorb and deactivate fecal proteolytic enzymes to purportedly prevent diaper rash. These clays are created by modification of well-known clays with long-chain organic amphiphilic compounds, such as long-chain quaternary armines. A diaper fabric incorporating the organophilic clay or a diaper containing organophilic clay dispersed in a superabsorbent polymer is suggested. The ability of unmodified clays to adsorb fecal enzymes was not described. The organophilic clays were incorporated into various pharmaceutically suitable vehicles, such as lotions, emulsions, creams, gels, and other aqueous vehicles. The vehicle, however, must be inert with respect to the organophilic clay and therefore be devoid of substances that bind to the clay and inactivate its ability to bind fecal enzymes. In particular, substances with hydrocarbon chains of C-8 and longer should be excluded from the composition. This restriction limits the inclusion of lipophilic skin health benefit agents that may, for example, enhance skin barrier function, moisturize and/or nourish the skin.

Various lipophilic compositions have been described for the prevention of diaper rash. Typically, barrier creams, lotions or ointments that contain these lipophilic skin health benefit agents are used to provide a barrier on the skin and treat skin conditions such as diaper rash. Typical lipophilic skin health benefit agents include petrolatum, mineral oil, natural oils and fatty acids. While these compositions can enhance the barrier properties of the skin, in many instances the application of these chemistries to the skin can be messy and inconvenient. They are also typically used only when signs of diaper rash are visually present.

Diaper liners may be treated with lipophilic skin health benefit agents, such as petrolatum, which can be transferred to the skin through normal diapering practices. Once transferred to the skin, diaper liner formulations may provide a barrier against feces and urine. These formulations may require high concentrations of petrolatum to ensure sufficient transfer to the skin for a health benefit. High concentrations of petrolatum can be messy, greasy to the touch, and may impair the fluid handling properties of an absorbent article, such as a diaper. The slow penetration of petrolatum into the skin can lead to smearing of the agent over the skin and onto clothes and other materials.

Based on the above-mentioned limitations, compositions are needed that adsorb irritants in biological fluids, such as fecal enzymes, and are compatible with lipophilic compositions that may improve skin health by other mechanisms. None of the above mentioned approaches to preventing diaper rash have explored the combination of lipophilic chemistries with particulate agents to adsorb enzymes and thus prevent skin inflammation, such as diaper dermatitis. Furthermore, the ability of unmodified clay particles to bind fecal enzymes has not previously been described.

SUMMARY OF THE INVENTION

The present invention provides that lipophilic chemistries and particulate skin irritant sequestering agents, such as non-organophilically modified clays, work synergistically to provide superior enzyme binding characteristics, and thus prevent damage to skin. These compositions can be used as superior diaper rash preventing agents and their incorporation into absorbent articles, such as diapers, allows for transfer of the beneficial agents to the skin.

Therefore, the present invention provides methods of using absorbent personal care articles, such diapers and adult incontinent briefs, comprising an absorbent article and having disposed thereon a skin irritant sequestering effective amount of non-organophilically modified particulate skin irritant sequestering agent and a lipophilic skin health benefit agent.

The present invention provides that the combination of particulate skin irritant sequestering agents and lipophilic skin health benefit agents provides a superior ability to adsorb, or sequester, irritants in biological materials, such as fecal enzymes, and prevent inflammatory skin diseases caused by said irritants, such as diaper dermatitis. The adsorption, or sequestration, of these irritants prevents their penetration into the skin where they cause skin damage and inflammation. A composition suitable for practicing the method of this invention comprises a skin irritant sequestering effective amount of a non-organophilically modified clay, such as bentonite or laponite, in combination with a lipophilic skin health benefit agent, such as petrolatum.

In a further embodiment of the invention, particulate sequestering agents in combination with various lipophilic skin health benefit agents demonstrate a synergistic effect. Lipophilic skin health benefit agents include petrolatum, steric acid, isoparrafins, various emollients, sterols, fatty acids, triglycerides and waxes, for example. A further embodiment of the method of this invention includes using absorbent articles wherein said compositions are incorporated on the body facing material of disposable absorbent articles, such as diapers, training pants, adult incontinent products, underpants, feminine care products and the like.

DETAILED DESCRIPTION OF THE INVENTION

Figure 1:
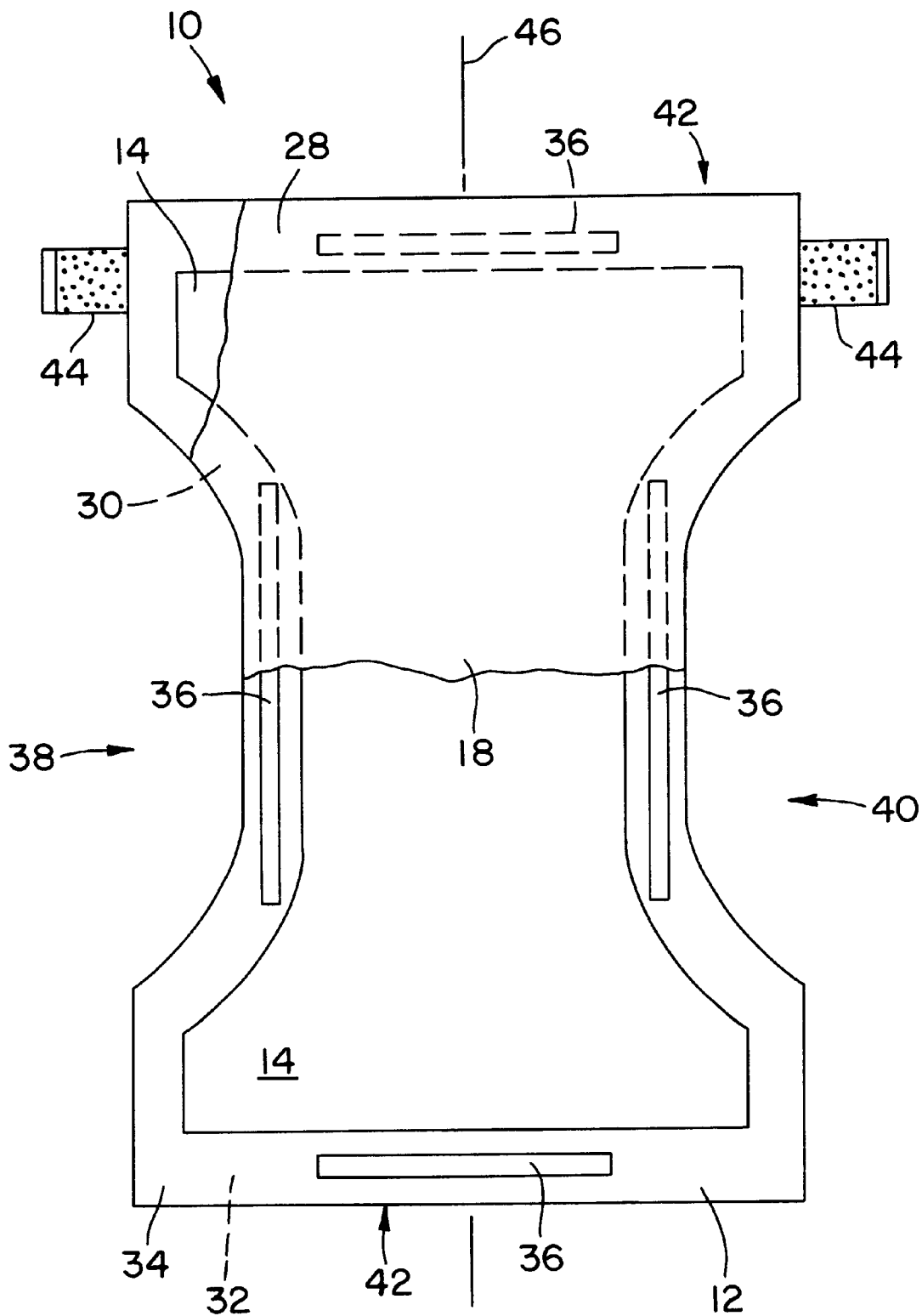
FIG. 1 representatively shows a partially cutaway, top plan view of an absorbent article according to one embodiment of the present invention.

Methods of using absorbent personal care articles, such a diapers and adult incontinent briefs, comprising an absorbent article and having disposed thereon a skin irritant sequestering effective amount of an unmodified particulate skin irritant sequestering agent and a lipophilic skin health benefit agent are provided.

The present invention provides novel methods of using absorbent products to adsorb, or sequester bodily waste skin irritants, such as fecal enzymes, to provide skin health benefits. In particular, it has been found that the novel combination of unmodified clay particles with lipophilic skin health benefit agents, such as petrolatum, can adsorb fecal enzymes and thus prevent them from penetrating into skin and causing skin inflammation.

As used herein, the term "sequestering agent" means a material that can adsorb a target molecule, such as a fecal protease, by covalent or non-covalent mechanisms. In certain embodiments, the affinity for the irritant is high, rapid, and irreversible. Adsorption of the irritant to the sequestering agent should preclude or significantly diminish the ability of a target irritant to penetrate into, and potentially through, the stratum corneum. As used herein, the term "sequestration" is defined as the process of binding of an irritant to a sequestering agent, by covalent or non-covalent mechanisms.

The amount of sequestering agent, such as a clay, and lipophilic skin health benefit agents applied to the article is not critical and can be routinely determined given the present disclosure, provided that a sufficient quantity is used to produce an effective decrease in skin damage and inflammation caused by skin irritants, such as fecal enzymes. Typically, the amount of unmodified particulate, such as clay, used on the article is such that when applied to the skin at least 50 ug/cm$^2$ is transferred to the skin.

The adsorption of fecal proteases to sequestering agents minimizes their ability to penetrate into the skin and cause skin irritation. The sequestering agent may be of sufficient size or charge that precludes its penetration into the skin. Thus, any protease adsorbed to the surface of the sequestering agent would not be expected to act underneath the surface of the skin and cause skin damage and inflammation.

This benefit may also be realized by using materials within an absorbent structure that have sequestering agent(s) bound thereto. In this case, the benefit is realized by binding irritants to the absorbent structure itself. The binding of skin irritants to the materials of the absorbent structure will again afford skin health benefits. It will be apparent to the artisan that the two approaches of binding skin irritants to sequestering agents deposited on the skin or binding them to sequestering agents on the product are not mutually exclusive strategies.

It has now been found that a particularly suitable sequestering agent is a readily available clay, in particular bentonite clay or laponite clay (Southern Clay Products, Inc.). Sequestration can also be achieved using many well-known particulate materials such as adsorbent clays, silica, titanium dioxide ($TiO_2$), hydroxyapatite, alumina, refractory metal oxides, or ion-exchange resins. Examples of suitable clays for use as sequestering agents include, but are not limited to, bentonite, laponite, montmorillonite, beidelite, hectorite, saponite and stevensite. Native, unmodified, sequestering agents (such as clays, silicas, and $TiO_2$, for example) can be used for binding relatively charged proteinaceous irritants, such as fecal proteases.

Additionally, the sequestering agents of the present invention are non-organophilically modified. As used herein, "organophilically modified" describes a compound that has been treated with long-chain organic amphiphilic compounds such as quaternary amines which results in exchange of the alkali metal ions by cationic organic molecules. For example, modification of a sequestering agent, such as clay, with one or two long-chain substituents, e.g. 14–20 carbon atoms, and two or three short-chain substituents such as methyl groups is an organophilic modification. Non-organophilically modified sequestering agents can include minor other processing modifications, such as the addition of inorganic counter ions, such as mono- and di-valent cations, e.g. lithium, sodium or potassium. Sequestering agents that are described as being "unmodified" with long-chain organic amphiphilic compounds are intended to encompass compositions of sequestering agents that have been treated with de minimus or insubstantial amounts of organophilic modification for the purpose of attempting to avoid infringement of the claims.

As used herein, the phrase "lipophilic skin health benefit agent" is defined as any substance that has a higher affinity for oil over water and provides a skin health benefit by directly interacting with the skin. Suitable examples of such benefits include, but are not limited to, enhancing skin barrier function, enhancing moisturization and nourishing the skin.

The lipophilic skin health benefit agents may include stearic acid, isoparrafin, petrolatum, and a combination thereof. The lipophilic skin health benefit agent can also be selected from fatty acids, fatty acid esters, fatty alcohols, triglycerides, phospholipids, mineral oils, essential oils, sterols, sterol esters, emollients, waxes, and a combination thereof. In some embodiments, the lipophilic skin health benefit agent has an average hydrocarbon chain with length greater than eight carbons (C-8). An example of a lipophilic skin health benefit lotion composition is commercially available as Vaseline® Intensive Care Lotion (Chesebrough-Pond's, Inc.).

As used herein, suitable lipophilic skin health benefit agents include, but are not limited to, the following materials classified according to CTFA designations:

Fats and Oils: Apricot Kernel Oil, Avocado Oil, Babassu Oil, Borage Seed Oil, Butter, $C_{12}$–$C_{18}$ Acid Triglyceride, Camellia Oil, Canola. Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Cherry Pit Oil, Chia Oil, Cocoa Butter, Coconut Oil, Cod Liver Oil, Corn Germ Oil, Corn Oil, Cottonseed Oil, $C_{10}$–$C_{18}$ Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated $C_{12}$–$C_{18}$ Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lanolin and Lanolin Derivatives, Lard, Lauric/Palmitic/Oleic Triglyceride, Lesquerella Oil, Linseed Oil, Macadama Nut Oil, Maleated Soybean Oil, Meadowfoam Seed Oil, Menhaden Oil, Mink Oil, Moringa Oil, Mortierella Oil, Neatsfoot Oil, Oleic/Linoleic Triglyceride, Oleic/Palrnitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Gil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalinitin, Trisebacin, Tristearin, Triundecanoin, Vegetable Oil, Walnut Oil, Wheat Bran Lipids, Wheat Germ Oil, Zadoary Oil, and the like, as well as mixtures thereof.

Fatty Acids: Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Paliitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

Fatty Alcohols: Behenyl Alcohol, $C_9$–$C_{11}$ Alcohols, $C_{12}$–$C_{13}$ Alcohols, $C_{12}$–$C_{15}$ Alcohols, $C_{12}$–$C_{16}$ Alcohols, $C_{14}$–$C_{15}$ Alcohols, Caprylic Alcohol, Cetearyl Alcohol, Cetyl Alcohol, Coconut Alcohol, Decyl Alcohol, Hydrogenated Tallow Alcohol, Lauryl Alcohol, Myristyl Alcohol, Oleyl Alcohol, Palm Alcohol, Palm Kernel Alcohol, Stearyl Alcohol, Tallow Alcohol, Tridecyl Alcohol, and the like, as well as mixtures thereof.

Essential Oils: Anise Oil, Balm Mint Oil, Basil Oil, Bee Balm Oil, Bergamot Oil, Birch Oil, Bitter Almond Oil, Bitter Orange Oil, Calendula Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmnine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, Sambucus Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof.

Sterols and/or Sterol Derivatives: As used herein, suitable sterols and sterol derivatives include, but are not limited to, the following materials:. sterols having a tail on the 17 position and having no polar groups for example cholesterol, sitosterol, stigmasterol, and ergosterol, as well as, $C_{10}$–$C_{30}$ cholesterolalanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, avocadin, sterol esters, and the like, as well as mixtures thereof.

Emollients: As used herein, suitable emollients include, but are not limited to, the following materials: Mineral Oil, Mineral Jelly, Petrolatum, cosmetic esters, fatty esters, glyceryl esters, alkoxylated carboxylic acids, alkoxylated alcohols, fatty alcohols, lanolin and lanolin derivatives, petrolatum base oils, silicones, fats, hydrogenated vegetable oils, polyhydroxy esters, and the like, as well as mixtures thereof.

Waxes: As used herein, suitable waxes include, but are not limited:to, the following materials: natural and synthetic waxes, such as bayberry wax, beeswax, $C_{30}$ alkyl dimethicone, candelilla wax, carnuaba, ceresin, cetyl esters, hydrogenated cottonseed oil, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, motan acid wax, motan wax, ouricury wax, ozokerite, paraffin, PEG-6 beeswax, PEG-8 beeswax, rice bran wax, shellac wax, spent grain wax, steryl dimethicone synthetic beeswax, synthetic candelilla wax, synthetic carnuba wax, synthetic japan wax. Synthetic jojoba wax, synthetic wax, and the like, as well as mixtures thereof. The preferred waxes include but are not limited to; carnuba, cerasin, cetyl esters, mnicrocrystalline wax, montan wax, ozokerite, synthetic wax, and the like, as well as mixtures thereof.

Humectants may also be included in the composition to provide an enhanced barrier and/or skin moisturization benefit. Humectants are typically cosmetic ingredients used to increase the water content of the top layers of the skin. This group of materials includes primarily hydroscopic ingredients. As used herein, suitable humectants include, but are not limited to, the following materials Acetamide MEA, Aloe Vera Gel, Arginine PCA, Chitosan PCA, Copper PCA, Corn Glycerides, Dimethyl Imidazolidinone, Fructose, Glucamine, Glucose, Glucose Glutamate, Glucuronic Acid, Glutamic Acid, Glycereth-7, Glycereth-12, Glycereth-20, Glycereth-26, Glycerin, Honey, Hydrogenated Honey, Hydrogenated Starch Hydrolysate, Hydrolyzed Corn Starch, Lactamide MEA, Lactic Acid, Lactose Lysine PCA, Mannitol, Methyl Gluceth-10, Methyl Gluceth-20, PCA, PEG-2 Lactamide, PEG-10 Propylene Glycol, Polyamino Sugar Condensate, Potassium PCA, Propylene Glycol, Propylene Glycol Citrate, Saccharide Hydrolysate, Saccharide Isomerate, Sodium Aspartate, Sodium Lactate, Sodium PCA, Sorbitol, TEA-Lactate, TEA-PCA, Urea, Xylitol, and the like, as well as mixtures thereof.

The composition used in this invention may also include emulsifying surfactants. The surfactants include, but are not limited to, sorbitan monoleate, sorbitan seequioleate, sorbitan trioleate, glyceryl stearate, sorbitan stearate, sorbitan tristearate, and the like, as well as mixtures thereof.

The composition used in this invention may also include viscosity enhancers. As used herein, suitable viscosity enhancers include, but are not limited to, the following materials: the group consisting of polyolefin resins, polyolefin polymers, ethylene/vinyl acetate copolymers, polyethylene, and the like, as well as mixtures thereof. Lipophilic skin health benefit agent lotion compositions can include humectants, surfactants, and viscosity enhancers present in an amount ranging from about 0.1% to about 10.0% of the total weight of the lipophilic skin health benefit agent composition.

It will be apparent to those skilled in the art that additional agents may be desirable for inclusion in the composition used in the present invention. Examples include, but are not limited to, acceptable carriers, anti-inflammatories, antimicrobials, anti-puretics, skin protectants, buffering agents, α-hydroxy acids, microbial or algal extracts and/or fractions thereof, enzyme inhibitors, antihistamines, antioxidants, analgesics, antioxidants, astringents, fragrances, dyes, natural and/or synthetic vitamin analogs, sunscreens, deodorants, and combinations thereof.

In still another aspect, the present invention resides in an absorbent article having a topsheet that includes a lotion formulation comprising the lipophilic skin health benefit agent(s) and the skin irritant sequestering agent on the outer body facing surface thereof.

In a particular embodiment, the body facing material of the absorbent articled used in the invention includes a lotion formulation wherein the lotion formulation comprises from about 5.0 to about 95.0 weight percent a lipophilic skin health benefit agent or mixture thereof, 0.1 to 25.0 weight percent a particulate skin irritant sequestering agent, and optionally, from about 0.1 to about 25.0 weight percent a viscosity enhancer, based on the total weight of the lotion. The lotion formulation may be applied by known methods in the art such as spraying, slot coating or printing.

As used herein, the term "body facing material" includes, but is not limited to, materials such as: body side liner; elastic material; tissue; intake and distribution material, absorbent material, including, but not limited to coform, woven and nonwoven materials, back sheet liner material, or any other material known in the art that are or can be used in the construction of personal care absorbent articles, such as diapers, training pants, absorbent underpants, adult incontinence product, feminine hygiene products. The term 'body facing material' is understood to include materials that are both ty pically and less frequently in contact with the wearer's skin. The body facing material of the present invention can be a single layer or multi-layers.

The composition used in the present invention can be applied to a specific portion or component of the absorbent article or to the entire surface of the absorbent article that comes into contact with the wearer's skin during use of the absorbent article. In addition, the composition can be applied in varying concentration or deposition amounts on the skin contacting surface of the absorbent article or portion thereof. The compositions are applied such that the compositions can be delivered via contact with the user's skin during the use of the absorbent article. The compositions used in the present invention can be applied after the body facing material has been incorporated into the absorbent article or prior to incorporating the body facing material into the absorbent article. The phrase "effective amount" of the composition is understood to mean an amount of the composition of the present invention which, when applied to the body facing material, will be effective in sequestering skin irritants, such as fecal enzymes.

As used herein, the term "absorbent article" refers to articles or products that are used to absorb and contain bodily fluids. Disposable absorbent articles 10 include such products as diapers, training pants, adult incontinence articles, absorbent under pants, and feminine care products that have been used to absorb body fluids and leave the skin dry.

Figure 2:
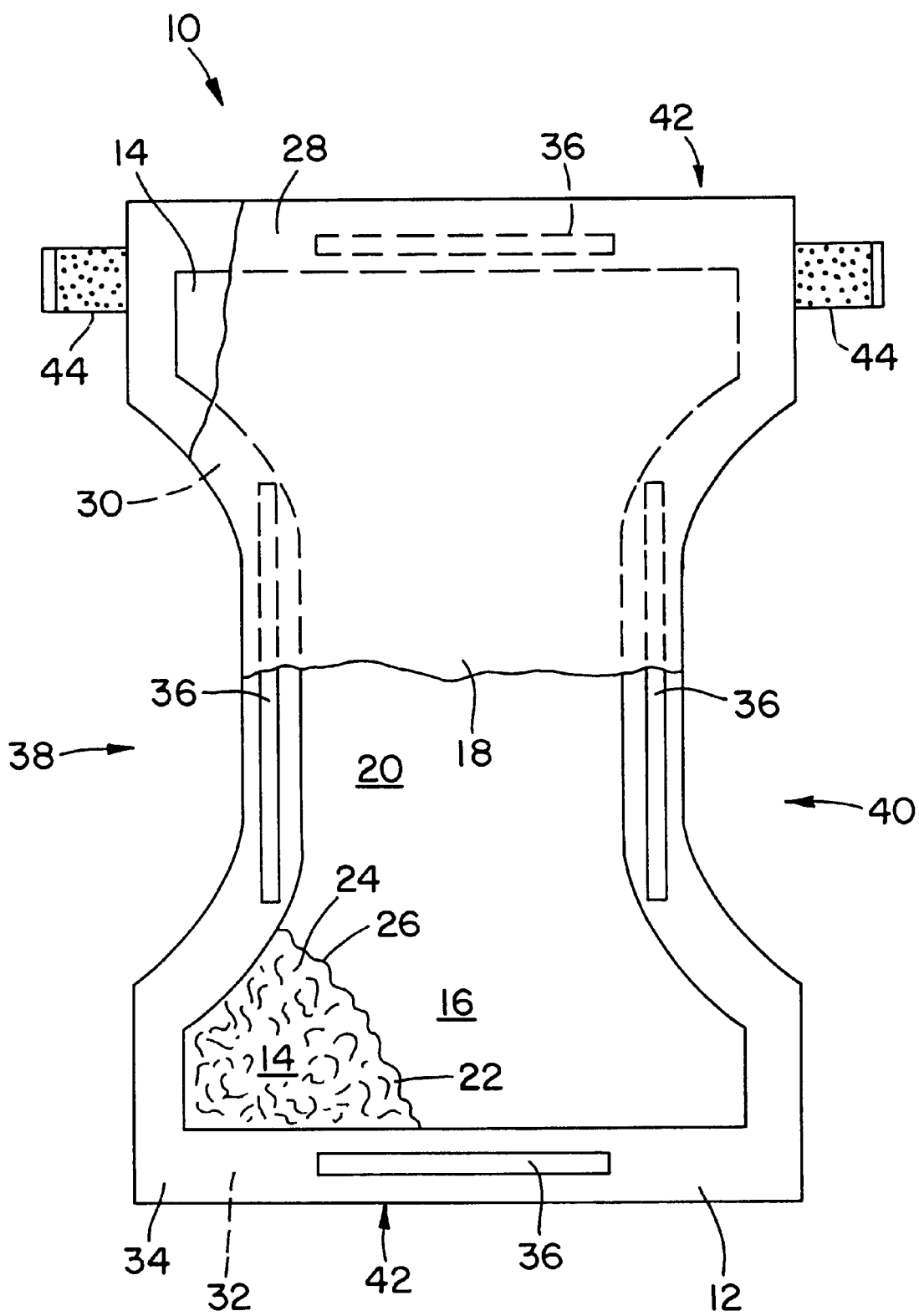
FIG. 2 representatively shows a partially cutaway, top plan view of an absorbent article according to another embodiment of the present invention.

Disposable absorbent articles 10 of this type generally comprise a liquid impermeable back sheet member 12, an absorbent core 14 or absorbent assembly 16, and a liquid permeable bodyside liner 18. (See FIGS. 1 and 2.) It is the bodyside liner 18 or the tissue material 20 that comes into contact with the wearer's skin. Typically, the back sheet member 12 is joined to the bodyside liner 18 with the absorbent core 14 disposed between the back sheet member 12 and the bodyside liner 18. A general description of these components, the back sheet member 12, the bodyside liner 18, and the absorbent core 14, will be discussed below.

In general, the absorbent core 14 absorbs and retains bodily fluids, such as urine, menses, and other body exudates. The absorbent core 14 is preferably compressible, conformable, and non-irritating to the wearer's skin. The absorbent core 14 may take a variety of sizes and shapes, such as rectangular, oval, hourglass, "T" shaped, asymmetric, dog bone, and the like. The absorbent core 14 may be comprised of a wide variety of liquid absorbent materials commonly used in absorbent articles 10. Absorbent cores 14 typically include a porous fibrous matrix 22 and high absorbency material 24.

The porous fibrous matrix 22 of absorbent core 14 is preferably an air laid batt of fluff and high absorbency material 24 which may be formed in many ways, for example according to the teaching of Mazurak and Fries as set forth in U.S. Pat. No. 4,381,782 the entire disclosure of which is incorporated herein by reference to the extent it is consistent herewith. The absorbent core 14 can comprise an air-formed mixture of high absorbency material 24 (SAP) and fibers 22, preferably of fluff pulp. The mixing of the fluff fibers 22 and the high absorbency material 24 can be homogeneous, graduated, or layered. Also, the fibers 22, other than fluff pulp such as chemically stiffened and thermo-mechanical pulps, can be used.

In addition, the absorbent core 14 can comprise absorbent material other than air formed fluff 22 and SAP 24. For example, coform materials as referenced in U.S. Pat. Nos. 4,818,464 to Lau and 4,100,324 to Anderson can be used to make the absorbent as long as they also contain high absorbency materials. In addition, wet formed composite materials comprising a combination of fibers and high absorbency materials as disclosed in U.S. Pat. No. 5,651,862 to Anderson et al. can also be used. Stabilized air-laid materials comprising a mixture of fibers, binder fibers, and high absorbency materials which are bound together by latex binding or through air bonding are also usable as absorbent materials. Additionally, any material known in the art that serves to absorb body exudates can be used to construct the absorbent core 14 as shown in the present invention.

The high absorbency materials 24 are typically hydrogel polymers that are desirably sufficiently cross-linked to render the materials substantially water-insoluble. Cross-linking may, for example, be by irradiation or by covalent, ionic, van der Waals or hydrogen bonding. Suitable materials are available from various commercial vendors, such as Dow Chemical Company (Drytech 2035 LD), Hoechst-Celanese Corporation and Allied-Colloid. Typically, the high-absorbency material 24 is capable of absorbing at least about 15 times its weight in water, and desirably is capable of absorbing more than about 25 times its weight in water.

The high-absorbency material 24 can be distributed or otherwise incorporated into the absorbent core 14 employing various techniques. For example, the high-absorbency material 24 can be substantially uniformly distributed among the fibers 22 comprising the absorbent core 14. The material 24 can also be non-uniformly distributed within the fibers 22 of the absorbent core 14 to form a generally continuous gradient with either an increasing or decreasing concentration of high-absorbency material 24, as determined by observing the concentration moving inward from the back sheet member 12. Alternatively, the high-absorbency material 24 can comprise a discrete layer separate from the fibers 22 of the absorbent core 14, or can comprise a discrete layer integral with the absorbent core 14.

The absorbent core 14 may also include a wrap layer 26 to help maintain the integrity of the fibrous absorbent core 14. (See FIG. 2.) This wrap layer 26 may comprise a cellulosic tissue or spunbond, meltblown or bonded-carded web material composed of synthetic polymer filaments, such as polypropylene, polyethylene, polyesters or the like or natural polymer filaments such as rayon or cotton. The wrap layer 26 may be made of the same materials as those used in the bodyside liner 18 or be made of materials differing from those used in the bodyside liner 18. In some cases, the bodyside liner 18 may be absent, and the wrap layer 26, also referred to as tissue material 20, will serve as the bodyside layer 18 of the absorbent article 10, coming in contact with the wearer's skin.

The absorbent core 14 can include additional components to assist in the acquisition, distribution, and storage of bodily exudates, such as a dusting layer, a transport layer, a wicking or acquisition/distribution layer, an intake layer, or a surge layer. See U.S. Pat. No. 4,798,603 to Meyer et al., or a surge management layer, such as described in U.S. Pat. No. 5,486,166 to Bishop et al., U.S. Pat. No. 5,364,382 to Latimer et al., U.S. Pat. No. 5,490,846 to Ellis et al., U.S. Pat. No. 5,429,629 to Latimer et al., U.S. Pat. No. 5,509,915 to Hanson et al., U.S. Pat. No. 5,192,606 to Proxmire et al.

The bodyside liner 18 consists of a nonwoven or other soft material for contacting the wearer's skin. The bodyside liner 18 has an outer (exterior) surface 28 that faces toward the wearer and an inner (interior) surface 30 that faces away from the wearer. The bodyside liner 18 is described in more detail below. The bodyside liner 18 is compliant and soft feeling to the wearer. The bodyside liner 18 may be any soft, flexible, porous sheet that is aqueous liquid permeable, permitting aqueous liquids to readily penetrate into its thickness. A suitable bodyside liner 18 may be manufactured from a wide range of materials, such as natural fibers (e.g., wood or cotton fibers), synthetic fibers (e.g., polyester or polypropylene fibers) or from a combination of natural and synthetic fibers or reticulated foams and apertured plastic films.

The bodyside liner 18 is formed of an aqueous liquid permeable material so that aqueous liquid waste, and possibly semi-solid waste as well, can pass through to the absorbent core 14 and be absorbed by the absorbent core 14 of the absorbent article 10. A suitable bodyside liner 18 may be comprised of a nonwoven web, a spunbond, meltblown or bonded-carded web composed of synthetic polymer filaments or fibers, such as polypropylene, polyethylene, polyesters or the like, a perforated film, or a web or natural polymer filaments or fibers such as rayon or cotton.

In addition, the bodyside liner 18 may be treated with a surfactant to aid in aqueous liquid transfer. Suitably, the bodyside liner 18 is a nonwoven spunbond. Suitably, the spunbond material is available from Kimberly-Clark Corporation, located in Roswell, Ga. The bodyside liner 18 has a weight from about 0.3 oz. per square yard (osy) to about 2.0 osy and alternatively about 0.5 osy. The bodyside liner 18 of the underpant maybe printed, colored or decoratively embossed. The bodyside liner 18 can also be a nonwoven web or sheet of polyolefm fibers, such as polypropylene, polyester, polyethylene, Rayon, chisso and the like. The bodyside liner 18 may also be a plastic film with perforations, an expanded plastic webbing material or a scrim material. The bodyside liner 18 has a pore size that readily allows the passage therethrough of air, sweat, and perspiration due to the breathability of the material. The bodyside liner 18 may be selectively embossed or perforated with discrete slits or holes extending therethrough.

Ideally, the fabric of the bodyside liner 18 is surface treated with a surfactant such as that commercially available from Union Carbide Chemicals and Plastics Company, Inc., of Danbury, Conn., U.S.A. under the trade designation TRITON X-102. As used herein, the term "fabric" refers to all of the woven, knitted and nonwoven fibrous webs. The term "nonwoven web" means a web of material that is formed without the aid of a textile weaving or knitting process.

As an alternate material, an aqueous liquid permeable bodyside liner 18 can be made of a carded web of polyester fibers bonded to a spunbonded polypropylene or polyethylene carrier sheet. The carded material is made up of about 20 to about 60 weight percent polypropylene or polyethylene and about 80 to about 40 weight percent polyester. The basis weight of this material can be between about 30 gsm and about 70 gsm.

The back sheet member 12 is needed to prevent aqueous liquid strike through to the outer clothing when bodily fluid is discharged onto the absorbent core 14 of the absorbent article 10. The back sheet member 12 typically consists of an aqueous liquid impermeable film such as polyethylene. The aqueous liquid impermeable back sheet member 12 has an outer (exterior) surface 32 that faces away from the wearer and an inner (interior) surface 34 that faces toward the wearer. In construction of the disposable absorbent article 10, the back sheet member 12, acting as a barrier, should retard the movement of the aqueous liquid through the absorbent article 10 by making the back sheet member 12 resistant to penetration normally encountered under wearing conditions. The back sheet member 12 desirably comprises a material that is formed or treated to be aqueous liquid impermeable.

Alternatively, the back sheet member 12 may comprise an aqueous liquid permeable material and other suitable means (not shown), such as an aqueous liquid impermeable layer associated with the absorbent core 14 may be provided to impede aqueous liquid movement away from the absorbent core 14 of the absorbent article 10. The disposable absorbent article 10 may be rendered aqueous liquid impermeable by any method well known in the art such as coating the absorbent core 14 or by securing a separate aqueous liquid impermeable material to the absorbent core 14. The back sheet member 12 may comprise a thin, aqueous liquid impermeable web or sheet of plastic film such as polyethylene, polypropylene, polyvinyl chloride or similar material. Other acceptable materials include a single spunbonded layer of the above types of materials, two layers of spunbonded and meltblown materials or a three-layer material of spunbonded-meltblown-spunbonded material. Suitable foam materials may also be used, as well as materials that are both aqueous liquid impermeable and vapor-permeable.

Alternately, the back sheet member 12 may comprise a nonwoven, fibrous web which has been suitably constructed and arranged to have low aqueous liquid permeability. Still alternately, the back sheet member 12 may comprise a layered or laminated material, such as a thermally bonded plastic film and nonwoven web composite. Alternatively, the back sheet member 12 consists of a aqueous liquid impermeable film or foam which is permeable to water vapor under normal wearing conditions. The back sheet member 12 has a water vapor transmission rate of at least about 800 grams/m$^2$/24 hours measured by ASTM E96-92. One example of a suitable film is a 39.4 grams per square meter microporous film produced by Mitsui and sold by Consolidated Thermoplastics (CT) under the tradename of ESPOIR® N-TAF-CT.

The absorbent articles 10 may also include elastic members 36 in the waist 42 (in absorbent articles 10 such as under pants and briefs), in the regions surrounding the leg openings 38 and 40, in the waist portions (not shown) as fit elastics (in absorbent articles 10 such as under pants), in side panels (not shown) (in absorbent articles 10 such as briefs and underpants), and in flap or, barrier structures (not shown). The elastic members 36 may be in the form of strips, ribbons, connected ribbons or strips, sheets, strands, bands, threads, filaments, or any combination of these shapes and others known to the art. The elastic members 36 may also be of latent elastic material that is activated after placement in the absorbent articles 10.

The compositions used in the present invention are solid or semisolid at 30 degrees C. As used herein, the term "semisolid" refers to a composition having a rheology typical of pseudoplastic or plastic fluids. Because the compositions are in at as least a semisolid state at ambient temperatures, migration of the composition is minimized. The compositions, being solid or semisolid at ambient temperatures, do not have the tendency to migrate into the interior of the bodyside liner 18 or the tissue material 20 and ultimately into the absorbent article 10 to which the composition has been applied. The compositions are transferable to the wearer's skin by normal contact, movement of the wearer, or the body heat of the wearer.

The bodyside liner 18 or the tissue material 20 contains an effective amount of the composition of the present invention. As used herein, the term "body facing material" is used interchangeably with the term "bodyside liner" and "tissue material". As used herein, the phrase "effective amount" of the composition refers to an amount of the composition which, when applied to a bodyside liner 18 or the tissue material 20, will be effective in reducing irritation.

The composition is applied to the outer surface 28 of the bodyside liner 18 or the tissue material 20 of the absorbent article 10. Any of a variety of application methods that evenly distribute lubricious materials having a molten or liquid consistency can be used. Suitable methods include spraying, slot coating, printing (such as flexographic printing), coating (such as gravure coating), extrusion, or combinations of these methods, such as spraying the composition on a rotating surface, then transferring the composition to the outer surface 28 of the bodyside liner 18 or the tissue material 20.

The manner of applying the composition to the bodyside liner 18 or the tissue material 20 should be such that the bodyside liner 18 or the tissue material 20 does not become saturated with the composition. If the bodyside liner 18 or the tissue material 20 becomes saturated with the composition, the fluid permeability of the bodyside liner 18 or the tissue material 20 may be reduced or blocked. In addition, saturation of the bodyside liner 18 or the tissue material 20 is not necessary to obtain therapeutic or protective benefits from the composition of the present invention.

A variety of fastening means 44 can be used for securing the absorbent article 10 around or in contact with the wearer including tape fasteners, belts, ties, disposable and reusable garments, and mechanical type fasteners. The mechanical type fasteners include buttons, button holes, snaps, buckles, clasps, hooks and loops, end extensions, tabs, and the like which are designed or adapted to interlock or engage some type of a complimentary device or the outer cover of the absorbent article 10. Suitable engaging elements for such mechanical closure elements include self-engaging geometric shaped materials, such as hooks, loops, snaps, buckles, bulbs, mushrooms, arrowheads, balls on stems, male and female mating components, or the like. In addition, elasticized fasteners are also used in assuring better fit of such absorbent articles 10. Examples of some fastening systems and securement members are disclosed in U.S. Pat. Nos. 5,423,789 to Kuen; 5,405,342 to Roessler et al.; 5,403,302 to Roessler et al.; 5,399,219 to Roessler et al.; 5,386,595 to Kuen et al.; 5,374,262 to Keuhn, Jr. et al.; 5,318,555 to Siebers et al.; 5,304,162 to Kuen; 5,288,546 to Roessler et al.; 5,176,671 to Roessler et al.; 5,176,671 to Roessler et al.; and, 5,019,073 to Roessler et al.

The disposable absorbent articles 10 used in the present invention may also include flap or gasket structures (not shown). These flap or gasket structures can be assembled in a number of different configurations, including those disclosed in U.S. Pat. No. 4,704,116 issued to Enloe, U.S. Pat. No. 4,846,823 issued to Enloe, U.S. Pat. No. 5,413,570 issued to Enloe, U.S. Pat. No. 5,415,644 issued to Enloe and U.S. Pat. No. 5,599,338 issued to Enloe.

The compositions used in the present invention may be applied to the entire outer surface 28 of the bodyside liner 18 or the tissue material 20 or portions thereof. Preferably, the composition is applied in a stripe or pattern aligned with a centered on the longitudinal centerline 46 of the disposable absorbent article 10. (See FIG. 1.) The dimensions of the stripe or pattern will vary with the different absorbent articles 10 to which the composition is being applied.

The compositions used in the present invention may be applied non-uniformly to the outer surface 28 of the bodyside liner 18 or the tissue material 20. The term "non-uniformly", as used herein, refers to the amount, pattern of distribution, thickness of the application, or the like, of the composition can be varied over the outer surface 28 of the bodyside liner 18 or the tissue material 20. The composition could be applied to the inner surface 30 of the bodyside liner 18 or the tissue material 20, alone or in combination with the application of the composition to the outer surface 28.

The compositions used in the present invention can be applied to the bodyside liner 18 or the tissue material 20 at any point during assembly of the absorbent article 10. For example, the raw material web being formed into the bodyside liner 18 or the tissue material 20 may be treated with the composition before the web is processed into the bodyside liner 18 or the tissue material 20; the bodyside liner 18 or the tissue material 20 may be treated with the composition before being incorporated into the absorbent article 10; and, the bodyside liner 18 or the tissue material 20 may be treated with the composition after the bodyside liner 18 or the tissue material 20 has been incorporated into the absorbent article 10.

EXAMPLES

Example 1

Unmodified Clays Sequester the Fecal Protease Trypsin from Solution

A. Bentonite

This example demonstrates the novel finding that unmodified clays can effectively adsorb, or sequester, irritating fecal enzymes.

Preparation of Stock Solutions

Porcine pancreatic trypsin (T-0134, Sigma Chemical Co, St. Louis Mo.) was prepared as a 4 µg/mL stock solution in Buffer A (50 mM sodium acetate, 150 mM NaCl, pH 5.5). Unmodified clay (bentonite, catalog #B-3378, Sigma Chemical Co., St Louis, Mo.) was prepared in the same buffer at a concentration of 4 mg/ml. After incubation at room temperature for at least 20 minutes to reconstitute the clay, working stock solutions of the bentonite were prepared at concentrations of 1, 2.5, 5, 10, 20, 40, and 80 µg/ml in Buffer A.

Sequestration Assay

Trypsin (500 µl stock) was added to 500 µl of one of the working bentonite stock solutions, mixed, and then incubated at room temperature for 15 minutes. The bentonite particles were then removed from the suspension by centrifugation at 14,000 rpm in an Eppendorf 5415C microcentrifuge for 5 minutes. Aliquots (10 µl) of the supernatant were removed for measurement of unbound enzyme.

Trypsin Assay

Unbound enzyme was assayed by quantifying the hydrolysis of the synthetic trypsin substrate Boc-Gln-Ala-Arg-AMC HCl, (Bachem, Inc. Catalog #I-1550) Reaction rates were determined by monitoring the hydrolysis of the substrate between 4 and 10 minutes at room temperature. The rate of hydrolysis was determined by measuring the liberated AMC fluorophore using a Fluoroskan Ascent microplate fluorometer (Labsytems, Inc.) equipped with 355 nm excitation and 460 nm emission filters.

Figure 3:
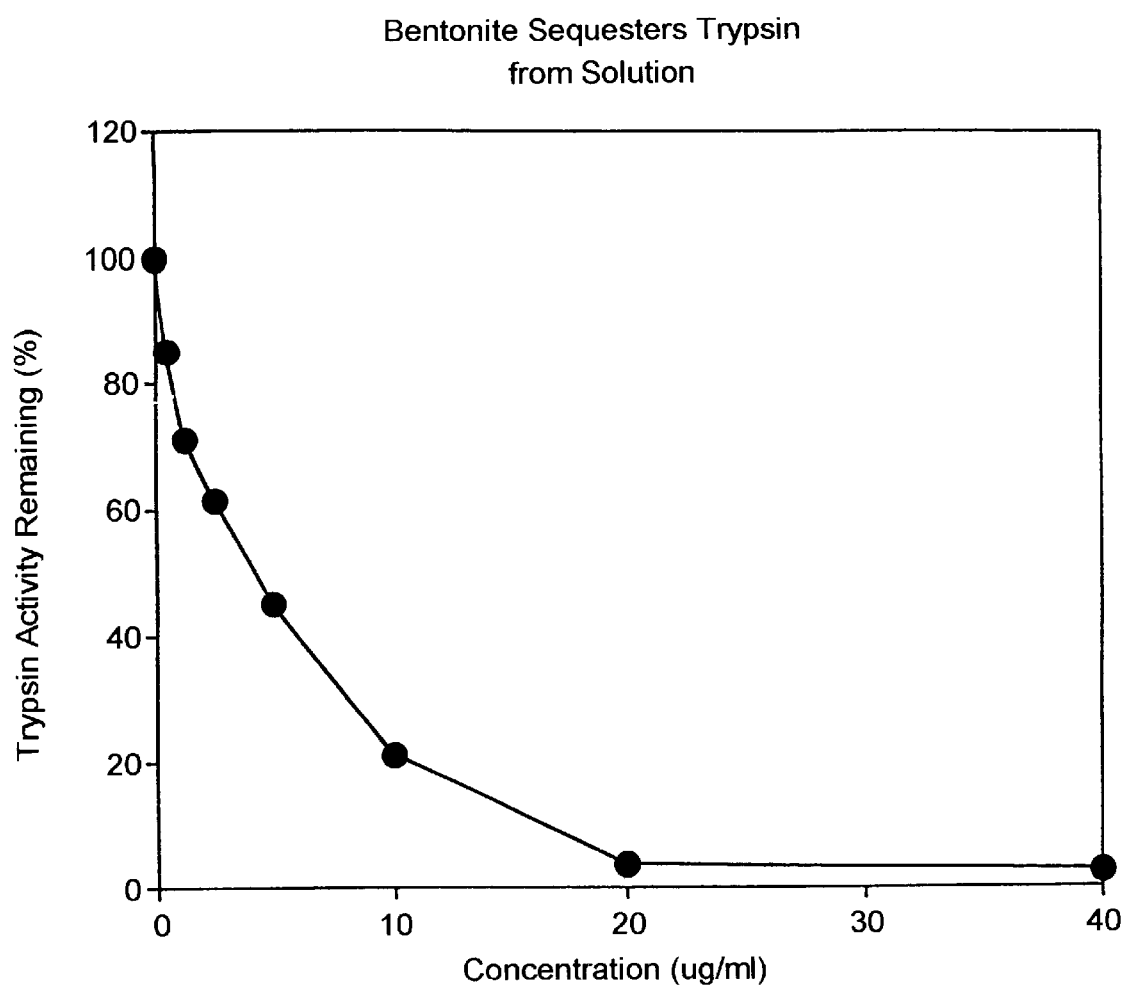
FIG. 3 representatively shows the sequestration of trypsin from solution by the unmodified clay bentonite.

As can be noted in FIG. 3, the unmodified clay bentonite effectively removes trypsin from a buffer solution.

B. Laponite

This example demonstrates the novel finding that laponite clay can effectively adsorb, or sequester, irritating fecal enzymes.

Preparation of Stock Solutions

Porcine pancreatic trypsin (T-0134, Sigma Chemical Co, St. Louis Mo.) was prepared as a 4 µg/mL stock solution in Buffer A (50 mM sodium acetate, 150 mM NaCl, pH 5.5). Unmodified clay (laponite, LAP-RD Micro Sample #12566-6/2028, Southern Clay Products, Inc. Gonzales, Tex.) was prepared in the same buffer at a concentration of 4 mg/ml. After incubation at room temperature for at least 20 minutes to reconstitute the clay, working stock solutions of the laponite were prepared at concentrations of 1, 2.5, 5, 10, 20, 40, and 80 µg/ml in Buffer A.

Sequestration Assay

Trypsin (500 ul stock) was added to 500 ul of one of the working laponite stock solutions, mixed, and then incubated at room temperature for 15 minutes. The laponite particles were then removed from the suspension by centrifugation at 14,000 rpm in an Eppendorf 5415C mnicrocentrifuge for 5 minutes. Aliquots (10 ul) of the supernatant were removed for measurement of unbound enzyme.

Trypsin Assay

Unbound enzyme was assayed by quantifying the hydrolysis of the synthetic trypsin substrate Boc-Gln-Ala-Arg-AMC HCl, (Bachem, Inc. I-1550) Reaction rates were determined by monitoring the hydrolysis of the substrate between 4 and 10 minutes at room temperature. The rate of hydrolysis was determined by measuring the liberated AMC fluorophore using a Fluoroskan Ascent microplate fluorometer (Labsytems, Inc.) equipped with 355 nm excitation and 460 nm emission filters.

Figure 4:
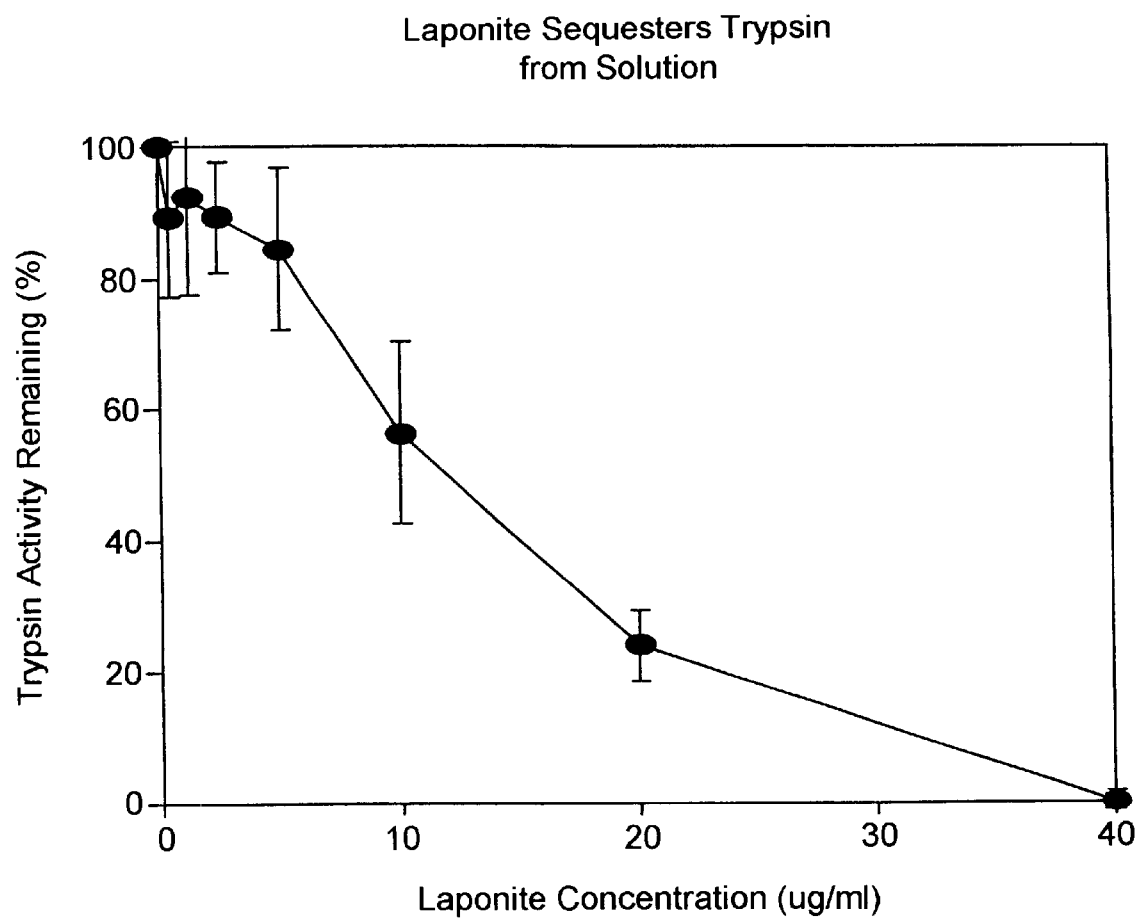
FIG. 4 representatively shows the sequestration of trypsin from solution by the unmodified clay laponite.

As can be noted in FIG. 4, the unmodified clay laponite effectively removes trypsin from a buffer solution. At a concentration of 40 µg/ml laponite, all of the 2 µg in the assay was effectively removed from solution.

Example 2

Laponite Reduces Skin Irritation Induced by a Fecal Extract in the Human Skin Model EpiDerm™

This example demonstrates how the unmodified clay laponite reduces the ability of infant fecal components to cause a pro-inflammatory response (release of interleukin-1 alpha) from a human skin model, EpiDerm™ (MatTek Corp., Ashland, Mass.).

Isolation of Infant Fecal Extract

Irritating fecal components were isolated from feces obtained from an infant experiencing diaper rash. The feces were suspended in water at a weight ratio of (1:5 feces:water) and vigorously mixed. Following mixing, the sample was centrifuged at 15,000×g for 20 min at 4° C. The supernatant was filtered through a 0.22 µM pore size cellulose acetate filter and stored at −80° C. until needed for the experiment. Trypsin activity was detected in the fecal extract according to the method in Example 1. The amount of activity detected corresponds to a 5850 picomoles/ml of bovine pancreatic trypsin. Elastase, an additional fecal protease, activity was also detected in the fecal extract. This enzyme was assayed by quantifying the hydrolysis of the substrate Ac-Ala-Ala-Pro-Ala-AMC (Bachem, Inc., Cat #I-1000). The amount of activity present corresponds to a concentration of 84 picomoles/ml of elastase.

In vitro Skin Irritation Assay

The skin model EpiDerm™, (MatTek, Cat. #EPI-200-HCF Lot No. 1343) (Ashland, Mass.) was used to assess the ability of particulate clays to prevent fecal protease-mediated skin inflammation.

The EpiDerm™ skin model was prepared according to the manufacturer's instructions. A 20 μL aliquot of laponite prepared in water at 0, 0.1, 0.5, 1 and 2% was applied to the skin surface. The EpiDerm™ was then incubated for 15 min in a 37° C. 5% $CO_2$ incubator. The fecal extract (20 μl) was then applied to the top surface of the EpiDerm skin model. Water was used as the negative control. After application of the treatments and controls, the skin model was incubated for 7 h at 37° C. and 5% $CO_2$. At the conclusion of the incubation period the underlying media was removed and the amount of interleukin 1-alpha quantified using an ELISA (R&D Systems, Minneapolis, Minn. Cat. #DLA50).

Figure 5:
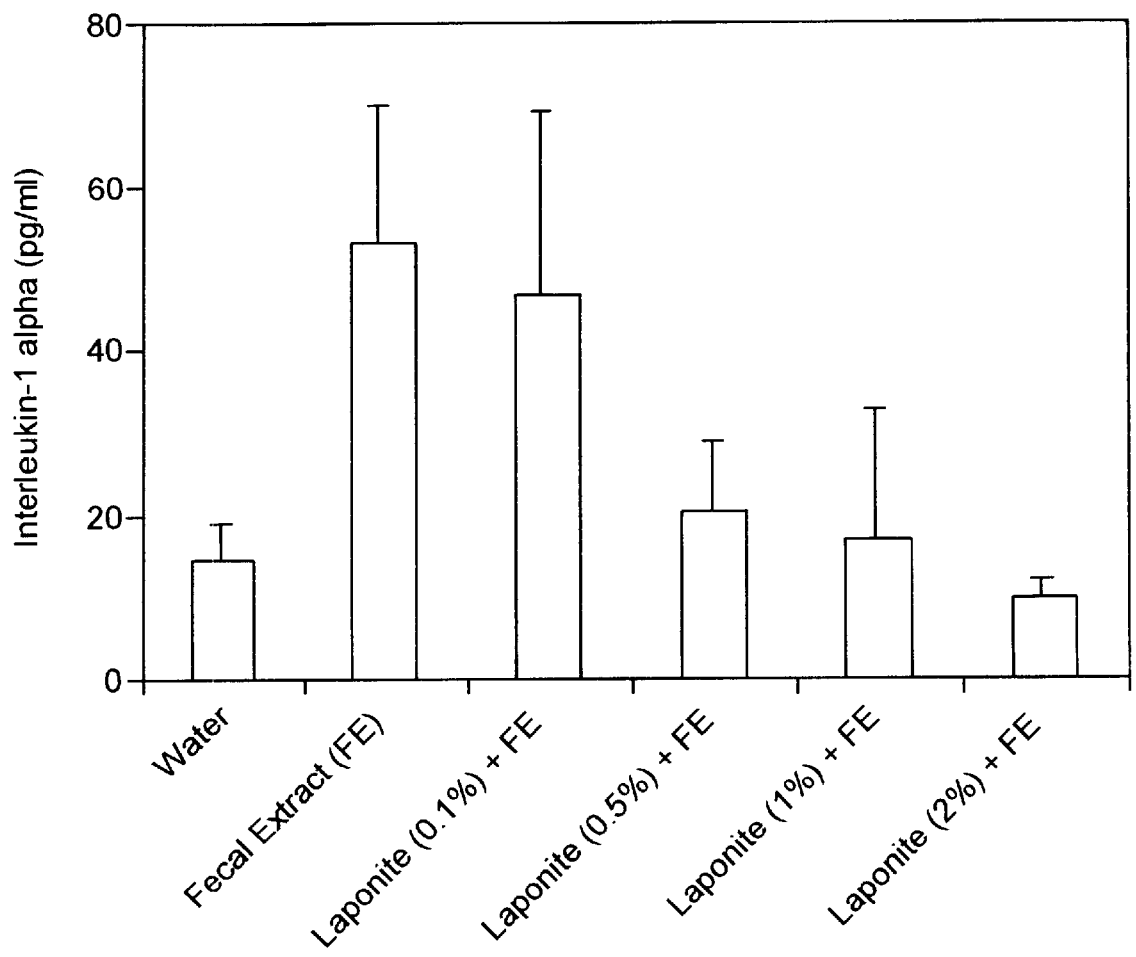
FIG. 5 representatively shows the reduction of skin irritation caused by an infant fecal extract by the unmodified clay laponite.
Figure 6:
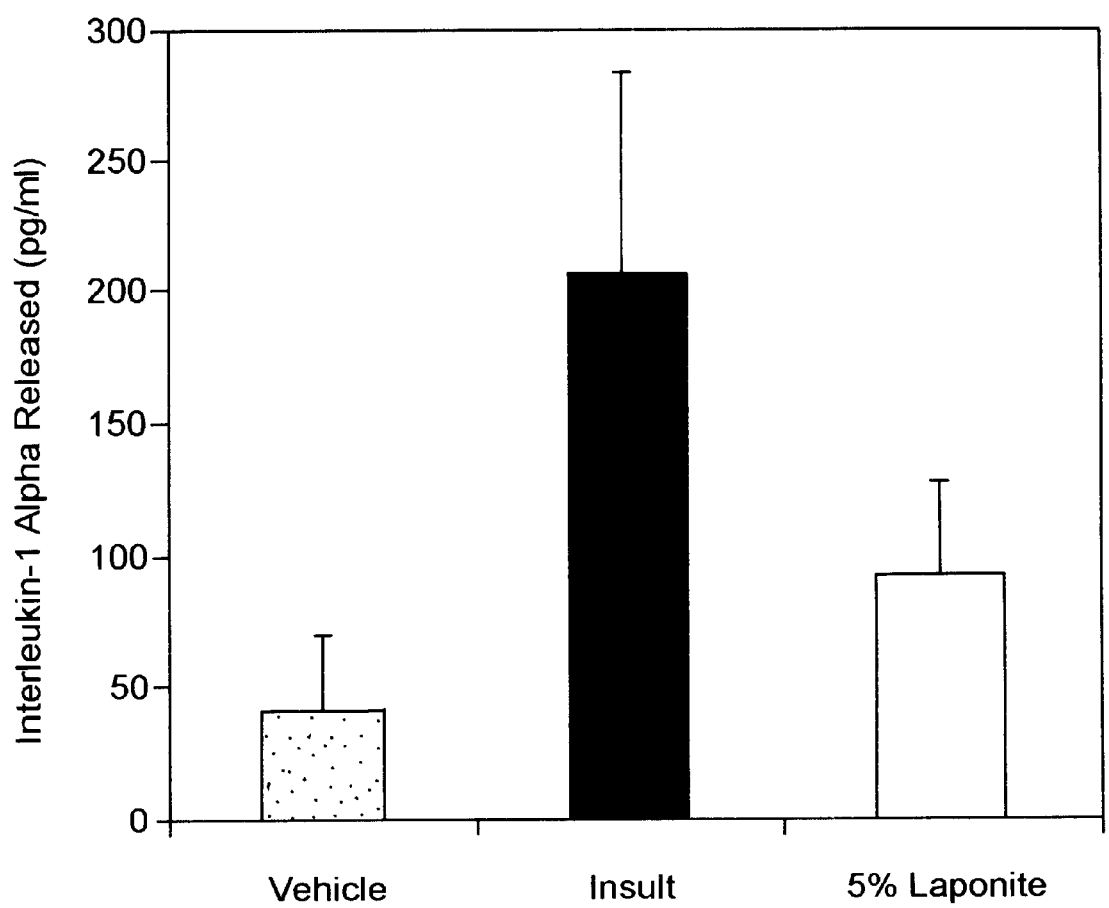
FIG. 6 representatively shows the reduction of skin irritation caused by a model fecal insult by the combination of the unmodified clay laponite with the lipophilic skin health benefit agent petrolatum.

As shown in FIG. 5, the unmodified laponite clay reduced the pro-inflammatory response caused by the fecal extract in the skin model. The decrease in interleukin-alpha release achieved statistical significance when 0.5, 1.0 and 2.0% laponite was added (Student's t-test, p<0.05). These data support the use of non-derivatized clays to improve skin health by sequestration of fecal irritants.

Example 3

Unmodifed Clays Effectively Sequester Fecal Enzymes when Formulated in a Lipophilic Skin Health Agent Experiments were conducted to illustrate that unmodified particulate sequestrants dispersed in a vehicle can bind proteases relevant to a diapered environment. Protease sequestration was determined by measuring protease removal from aqueous solutions exposed to petrolatum with and without sequestrants. Additionally, proteases labeled with fluorescent markers were used to permit direct visualization of protease binding to sequestrants dispersed in the petrolatum.

Preparation of Sequestrant/Petrolatum Dispersions

A 20 wt % dispersion of Laponite XLG (Southern Clay, Gonzales, Tex.) was prepared in petrolatum (Glenpure L: Glen Corporation, St Paul, Minn.) by low shear mixing at 50° C. followed by cooling. The resulting mixture was diluted with neat petrolatum to prepare lower wt % clay suspensions.

Sequestration Assay

Two gram samples of petrolatum with and without the inclusion of sequestrants were melted at 50° C. in an aluminum weighing pan 5 cm in diameter. A thin continuous film of petrolatum resulted upon cooling at ambient temperature. The samples were then exposed to solutions of a representative fecal protease. This was accomplished by adding 5 ml of trypsin (Sigma T-0134) to the pans at a concentration of 300 ng/ml in 10 mM TRIS buffered saline (pH=7.8; 150 mM NaCl). The solutions in the pans were sampled periodically to determine the protease activity present.

Protease Assay

Protease activity was determined using the EnzChek Protease Assay Kit available from Molecules Probes (Eugene, Oreg.; Cat #E-6638) following their recommended procedure. Briefly, 50 μl samples of known or unknown protease solutions were added to 4 ml of an aqueous solution containing 2.7 ng/inl of the fluorescently (BODIPY-FL) labeled casein. Hydrolysis of the fluorogenic casein substrate results in an increase in the solution's fluorescence. The fluorescence of the sample solutions was measured using a Turner D700 filter fluorometer (Molecular Probes, Eugene, Oreg.) at Ex/Em=495/515 nm at timepoints of interest. The amount of fluorescence is expressed in arbitrary units, Relative Fluorescence Units (RFU). Increasing rates of fluorogenesis corresponds to higher levels of protease activity in a sample. Protease activity present in a sample can be quantified by generating a standard curve where rates of fluorogenesis are determined for known concentrations of the protease of interest. The results are then expressed as the amount of protease necessary to give a similar fluorescent signal. Alternately, protease activity can be evaluated qualitatively by determining the change in RFU values as a function of time.

The ability of petrolatum containing either 0 or 10.0 wt % laponite to sequester protease from solution was determined using the methods outlined above. A control trypsin solution (3.7 ng/ml) that was not exposed to any formulation was also included in the experiment. Reduction of proteolytic activity was attributed to removal of enzyme from solution when decreases beyond that of the vehicle control (petrolatum devoid of sequestrant) were observed.

TABLE 1

Amount of active trypsin remaining in solution (ng/ml) vs time.

| Contact Time (hours) | Trypsin Control Solution | Petrolatum without laponite | Petrolatum with 10% laponite |
| --- | --- | --- | --- |
| 2 | 4.4 | 4.8 | 2.7 |
| 4 | 5.2 | 5.0 | 3.1 |
| 20 | 4.4 | 4.6 | 0.4 |

No differences were detected between a control trypsin solution and the trypsin solution contacting neat petrolatum. In contrast, a reduction in the proteolytic activity of the solution in contact with petrolatum containing laponite is detected relative to the controls after two hours of contact. After 20 hours, a ten-fold reduction in trypsin activity is measured for the solution contacting the clay-containing petrolatum relative to the controls.

Dose dependence of trypsin removal by laponite was determined using methods similar to those described above. Petrolatum samples containing between 0 and 20 wt % laponite were prepared. A solution containing 400 ng/ml of trypsin, in 10 mM TRIS buffered saline, was allowed to contact the petrolatum samples as described above. Following 20 hours of contact time, the amount of protease activity was determined. The amount of activity detected was used to quantify the amount of active trypsin remaining in solution.

TABLE 2

Binding of trypsin by laponite in petrolatum.

| Laponite present petrolatum (wt %) | Trypsin remaining solution (ng/ml) |
|---|---|
| 0.0 | 13.1 |
| 0.5 | 9.5 |
| 1.0 | 9.0 |
| 5.0 | 0.0 |
| 10.0 | 0.2 |
| 20.0 | 0.0 |

The laponite content in petrolatum required to remove all detectable trypsin from a 400 ng/ml solution is between 1.0 and 5.0 wt %. Levels of laponite as low as 0.5 wt % were sufficient to reduce the amount of trypsin detected in the solution.

Example #4

Laponite Dispersed in Petrolatum Reduces a Proinflammatory Response Induced by a Fecal Insult in a Human Skin Model, EpiDerm™

Laponite dispersed in petrolatum was evaluated for its ability to reduce a pro-inflammatory response induced by a fecal protease mix when applied to the human skin model, EpiDerm™ (MatTek Corp., Ashland, Mass.). A protease mix (trypsin-chymotrypsin, Speciality Enzymes and Biochemicals Co., Chino, Calif., Lot #809023, containing not less than 2,500 USP units/mg of trypsin and not more than 300 USP units/mg of chymotrypsin) stock solution was prepared at 10 mg/ml in 50 mM sodium acetate pH 5.5, and 0.15 M NaCl. The protease stock solution was diluted with phosphate-buffered saline (PBS), pH 7.4 (Cat #10010, Life Technologies, Gaithersburg, Md.) to 250 $\mu$g/ml and served as a fecal irritant insult.

The experiment was performed by applying a 15 $\mu$l aliquot of petrolatum containing 0.0% or 5% laponite to the surface of the EpiDerm skin model and gently spreading the treatments using a glass rod. The EpiDerm™ was then incubated for 30 min at 37° C. and 5% $CO_2$ in an incubator. The fecal irritant insult (10 g) was then applied to the petrolatum- and laponite-petrolatum-treated EpiDerm samples while a PBS vehicle was applied to another set of EpiDerm samples treated with petrolatum devoid of laponite. The skin model was returned to the same incubator referenced above for 6 hours. At the conclusion of the incubation period the underlying media was removed and the amount of IL-1$\alpha$ release was quantified using an ELISA (IL-1$\alpha$ Quantikine Kit; Cat. #DLA50, R&D Systems, Minneapolis, Minn.).

FIG. #6 illustrates the results of this experiment. Petrolatum containing 5% laponite showed a significant reduction in the pro-inflammatory response (IL-1$\alpha$ release) induced by the fecal irritant insult (Student's t-test, p<0.05) relative to the negative control. These data indicate that the delivery a non-derivatized clay such as laponite with a vehicle such as petrolatum can improve skin health when delivered to the skin's surface by neutralizing fecal irritants that can be present in the diapered environment.

Example 5

Labeled Trypsin Binds to Laponite Dispersed in Petrolatum and Retains its Activity This example demonstrates that the mode of action of unmodified clays in petrolatum is through adsorption of the enzyme to the particulate rather than direct inhibition of enzyme activity.

Laponite XLG (Southern Clay, Gonzales, Tex.) was dispersed in petrolatum (Glenpure L: Glen Corporation, St Paul, Minn.) by low shear mixing at 50° C. The resulting mixture contained (5%) laponite. The dispersion was cooled and exposed to trypsin (SIGMA #T-0134) that was labeled with the fluorophore Texas Red® (TR). Trypsin was labeled using a protein labeling kit (Molecular Probes Kit #F-6162) that attaches TR via a succinyimidyl ester. The procedure was performed in accordance with the procedure provided with the kit. A working solution of labeled protease was prepared by mixing one part labeled protease with approximately 100 parts of unlabeled enzyme dissolved in 10 mM TRIS buffered saline (pH=7.8; 150 mM NaCl). This working solution contained approximately 300 ng/ml protease and was used for fluorescent imaging. The petrolatum with laponite was then washed with the TBS buffer to remove superfluous trypsin. Subsequently, the sample was exposed to a fluorogenic trypsin substrate, (BODIPY-FL) labeled. casein (EnzChek Protease Assay Kit, Molecular Probes, Eugene, Oreg. Cat #E-6638). The sample was then washed and imaged as described in Example #7 except that the sample was imaged using excitation wavelengths of 495 nm and 595 nm for the BODIPY-FL and Texas Red fluorophores, respectively.

A gray scale version of the fluorescent photomicrographs that represent the results of this experiment was created (data not shown). Hydrolysis of the fluorogenic casein gives rise to green fluorescence when excited with 495 nm light. Red fluorescence is obtained when viewing the same sample excited with 595 nm light (data not shown). Under these conditions, the Texas Red will fluoresce Red.

Thus, the data demonstrates that the trypsin has bound to the particulate laponite when this sequestrant is delivered in a vehicle, petrolatum (data not shown). The data demonstrates that the trypsin remains active when bound to the sequestrant (data not shown). Taken together, the co-localization of labeled trypsin (red fluorescence) and hydrolyzed fluorogenic trypsin substrate (green fluorescence) in the same sample provides strong evidence that the dispersed clay sequesters active protease from a contacting aqueous solution and that the measurable decrease in protease content in aqueous solution is not due to direct inhibition of enzyme activity. Therefore, unmodified clay sequestrants in lipophilic skin health benefit agents, such as petrolatum, would be expected to adsorb, or sequester, fecal proteases and prevent their penetration into the skin.

Example 6

Synergistic Activity Between a Laponite Clay and a Lotion Vehicle Containing Lipophilic Skin Health Benefit Agents in Preventing Typsin Permeation Through a Skin Model This example demonstrates how unmodified clays not only maintain sequestration activity against fecal proteases in a lotion that contains various lipophilic skin health benefit agents with aliphatic chains greater than C-8 but also demonstrates how the lipophilic agents and the clay work synergistically to provide enhanced sequestration benefits.

The skin model EpiDerm™, (MatTek, Cat. #EPI-200-HCF Lot No. 1343) (Ashland, Mass.) was used in this experiment. Laponite clay (LAP RD MICRO Sample #12566-62028; Southern Clay Products, Inc.) and Vaseline®

Intensive Care Lotion (Extra Strength Formulation—Cheesborough-Ponds, Inc.) were evaluated alone and in combination for their ability to prevent the penetration of trypsin into the skin.

Ingredients present in Vaseline Intensive Care Extra Strength Lotion include (in order of decreasing concentration): water, glycerin, stearic acid, C11–13 isoparaffin, glycol stearate, triethanolamine, petrolatum, sunflower seed oil, glyceryl stearate, soya sterol, lecithin, tocopheryl acetate, retinyl palmitate, urea, collagen amino acids, sodium PCA, zinc oxide, cetyl phosphate, magnesium aluminum silicate, fragrance, stearamide AMP, corn oil, methylparaben, DMDM hydantoin, iodopropynyl butylcarbamate and disodium EDTA. Several of these components, in particular, stearic acid, C11–13 isoparaffin, petrolatum, sunflower seed oil contain hydrocarbon chains that contain greater than eight carbon units.

A 5.0% Laponite suspension was prepared by adding 5.0 g of Laponite to 10.0 ml of deionized water. The resulting solution was mixed for one half hour at room temperature on a rocking platform. At the conclusion of the mixing step 100 $\mu$l of the Laponite suspension was added to 900 $\mu$l of the Vaseline® Intensive Care Lotion (VICL). The resulting formulation was 0.90×VICL with 0.5% Laponite. Likewise, for the laponite alone control, 100 $\mu$l of the 5.05 Laponite solution was added to 900 $\mu$l of deionized water to yield a 0.5% Laponite in water.

Porcine pancreatic trypsin (Sigma Chemical Co. Cat. #T-0134) was prepared as a stock solution at 1 mg/ml in 10 mM acetate buffer pH 5.5 and stored at $-20°$ C. until used. The stock solution was thawed and diluted to 200 $\mu$g/ml in the Dulbeccos's Phosphate Buffered Saline provided by the manufacturer of EpiDerm™.

The EpiDerm™ skin model was prepared according to the manufacturer's instructions. Following pre-incubation, 10 $\mu$l samples of the treatments (VICL, VICL with 5.0% Laponite, or 5.0% Laponite) were applied to the surface of the skin model. The treatments were added with the aid of a volumetric positive displacement pipet. Following application the treatments were spread evenly over the surface of the skin model with the aid of glass rod that had rounded edges on the end. For the negative treatment control, nothing was added to the model. One to 2 minutes following the application of treatments 10 $\mu$l of the trypsin solution (200 $\mu$g/ml) was applied. All treatments were performed with n=six replicates. The EpiDerm skin model was incubated for 6 hours at 37° C. and 5% $CO_2$. At the conclusion of the incubation period the underlying media was collected and immediately transferred to a $-70°$ C. freezer until analyzed for trypsin content.

Quantification of trypsin was performed using quantitative densitometry of casein zymograms. Briefly, trypsin standards were prepared at concentrations of 2,000, 670, 200, and 20 ng/ml. Fifteen $\mu$l samples of the standards and unknowns were placed in Eppendorf tubes along with an equal volume of NOVEX 2×Tris-Glycine SDS sample buffer and incubated at room temperature for 10 minutes. A casein zymogram gel (NOVEX Cat. #EC6405) was placed in an electrophoresis tank (NOVEX #EI9001) filled with TRIS-Glycine SDS running buffer. Twenty-five $\mu$l samples of standards and unknowns were placed in each well of the gel. The samples were electrophoresed for 75 minutes at 125VDC. Following electrophoresis, the gels were processed per the vendor's instructions, stained with Coomassie R-250 colloidal blue stain and decolorized. The resulting gels were imaged with a pdi 325oe high-resolution color imaging system equipped with pdi Diversity One™ image analysis software. (Huntington Station, N.Y.). Densitometry was performed on the resulting image to develop a standard curve (trypsin concentration vs. the optical density of the attendant trypsin bands on the gel) using the trypsin standards. The concentration of trypsin present in the unknown samples was then determined using this standard curve. Differences in means were analyzed using the Student's t-test; the significance value was set at $P<0.01$.

Figure 7:
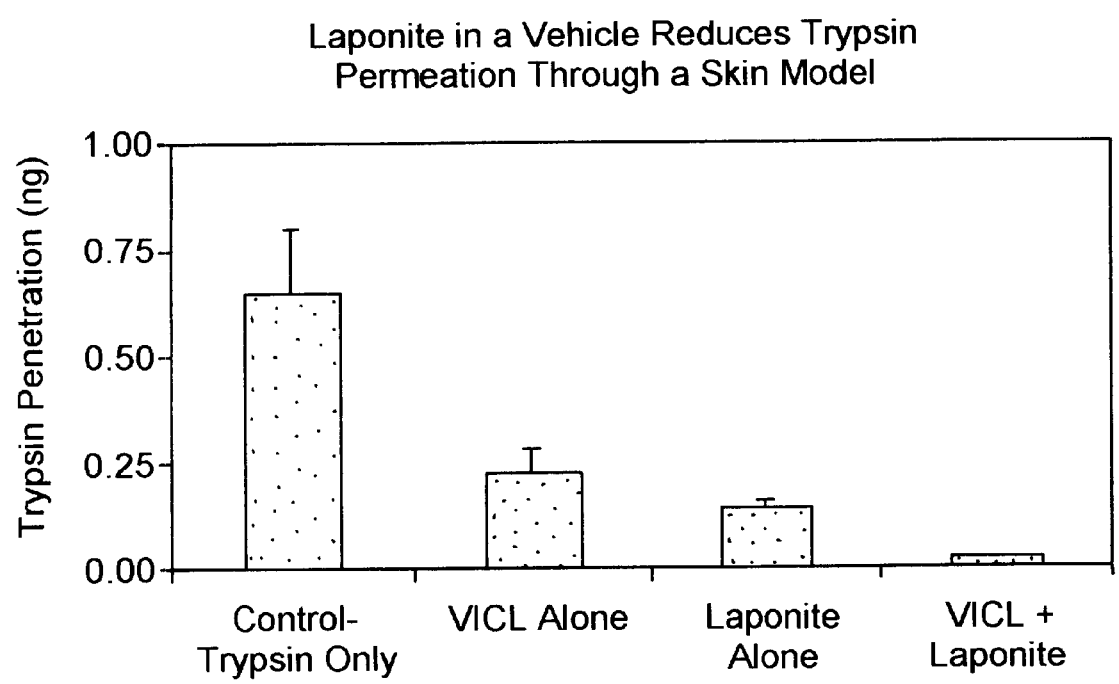
FIG. 7 representatively demonstrates the synergistic activity between unmodified clay (laponite) and a lotion containing multiple lipophilic skin health benefit agents in preventing trypsin penetration into skin.

FIG. 7 summarizes the results of this experiment. Pre-treating the skin model with the VICL formulation containing the lipophilic skin health benefit agents surprisingly reduced the penetration of trypsin through the skin model. Laponite clay was also effective in reducing the penetration of trypsin through the skin model. Surprisingly, the combination of VICL with the laponite caused a synergistic increase in the reduction of trypsin through the skin model. Therefore, FIG. 7 illustrates the unexpected finding that a synergistic activity exists between the lotion containing the lipophilic skin health benefit agents and the particulate (clay) sequestrant in reducing the penetration of skin irritants, such as trypsin, into the skin.

Thus, far from being an inert carrier, a vehicle can facilitate the activity of sequestrants. This is true even with vehicles that contain significant amounts of high molecular weight (C>8) aliphatic compounds. Synergistic activity between the sequestrant and the vehicle was unexpected as previous art suggests that vehicles of this type will inactivate the activity of irritant sequestrants Example 7

Unmodifed Clays Maintain Sequestrating Activity when Applied to Non-Woven Materials

7A

Bentonite and Laponite-Treated Nonwoven Materials Sequester the Fecal Protease Trypsin This example demonstrates how substrates, such as nonwovens, treated with unmodified clays effectively sequester the fecal protease trypsin. Polypropylene nonwoven materials were prepared with and without the inclusion of clay (laponite, 2.0 mg/$cm^2$ non-woven or bentonite, 1.5 mg/$cm^2$ non-woven). All non-woven materials were treated with Ahcovel surfactant to impart wettability to the resulting non-woven samples. Eight and 24 μg/rnL solutions of trypsin were prepared in Buffer A of Example 1. Disks (0.64 $cm^2$) of the non-woven materials were placed in microcentrifuge tubes along with 500 μl of Buffer A and 500 μl of either the 8 or 24 μg/mL trypsin solution. The resulting tubes were mixed on a rocking platform for 15 minutes at room temperature. The tubes were then centrifuged for 5 mnin at 14,000 rpm in an Eppendorf 5415C microcentrifuge and the supernatants assayed for trypsin activity as described in Example 1.

Relative fluorescence units were converted to ng/mL trypsin using a trypsin standard curve and the amount of trypsin in ng was calculated for the total well volume of 200 μl and adjusted for dilution. As shown in Table 3, both the bentonite-treated nonwoven and the laponite-treated nonwoven were effective in sequestering trypsin from solution. Non-woven control materials devoid of clay did not have any detectable affinity for trypsin (data not shown).

TABLE 3

Binding of Trypsin by Clay-treated Non-wovens

| Non-woven Treatment | Trypsin sequestered/clay on (ng/mg) |
|---|---|
| Laponite | 3,099 |
| Bentonite | 12,231 |

Example 7B

Adsorption of Trypsin by Laponite-treated Meltblown Fabric as Judged by Fluorescent Microscopy An experiment was performed that demonstrates that the reduction in soluble trypsin by clay-treated nonwoven materials is due to physical adsorption of the enzyme to the material. Meltblown polypropylene fabric was coated with Laponite (a synthetic layered silicate manufactured by Laporte Industries, Widnes, UK) using a chromatography reagent sprayer (VWR Scientific Products, Cat. #21428-352). A formulation containing 1 weight percent Laponite was prepared by stirring 1.0 g of Laponite into 100 mL of water for 20 minutes at room temperature in a beaker, until the contents appeared clear. Then 14 mL of a 5 wt % dispersion of sodium dioctyl sulfosuccinate (Aerosol TO) was added, resulting in a formulation containing 0.6% surfactant. The formulation was poured into a chromatography reagent sprayer (operated on 5 psi air pressure) and was sprayed onto the meltblown fabric (pinned to a cardboard backing) until the fabric appeared wet. The fabric was turned over and the spraying was repeated. The fabric was then dried at 50° C. for 1 hour. The spraying and drying process was repeated twice, for a total of three sprayings.

Porcine pancreatic trypsin (Sigma Chemical Co. Cat. #T-0134) was labeled with the fluorescent dye, Texas Red®. The Texas Red labeling was accomplished using the Fluo-Reporter Protein Labeling Kit (Molecular Probes catalog #F-6162) and following the instructions provided with the kit.

Five microliters of a 2.86 mg/ml solution containing the labeled trypsin was added to 5.0 mL of non-labeled trypsin at a concentration of 294 ug/ml. The resulting trypsin working solution had a trypsin concentration of approximately 300 ug/ml trypsin, 1% of which was labeled. The trypsin (both labeled and unlabeled) diluent was phosphate-buffered saline (0.01M phosphate buffer, 0.0027M potassium chloride, 0.137M sodium chloride, pH 7.4 at 25° C.).

Samples were evaluated for trypsin binding activity by placing a circular sample of laponite-treated meltblown inside a syringe filter assembly (1.7 cm in diameter). One ml of the trypsin working solution was drawn into a plastic syringe. The syringe filter assembly containing the treated meltblown was affixed to the end of the syringe, and the entire volume of the trypsin working solution was passed through the sample at a flow rate of approximately 4 ml per minute. The process was repeated with a sample that was devoid of laponite. The disks were washed thoroughly by passing 6 consecutive 1 mL portions of distilled water through the syringe filter, a total of 6 washes. The fabric was removed from the filter and air-dried on an absorbent paper towel.

Adsorption of trypsin to the treated nonwoven materials was determined by fluorescent microscopy. Square samples (approximately 2 $mm^2$) obtained from the disks described above were mounted on a microscope slide in Resolve® Microscope Immersion Oil (Low viscosity; VWR catalog #48218-061). The samples were observed through a Leica fluorescent microscope, DMIRB, equipped with a high-pressure mercury lamp for epi-fluorescence. Fluorescent imaging of labeled trypsin was accomplished using a 595 nm excitation filter and a 615 nm emission filter. The samples were observed at 160×magnification. The images were acquired digitally for documentation using a Hammatsu color chilled 3CCD camera (C5810). The acquired data was processed with Adobe Photoshop® image processing software.

Black and white images of the above described bright field image and the fluorescent image of the same nonwoven test material (data not shown) were obtained. This material resulted from applying Laponite to the nonwoven material with a spray apparatus. This material was then exposed to fluorescently labeled trypsin by passing a solution of labeled trypsin through the sample while it was housed in a syringe filter assembly, followed by copious washing of the material. No appreciable fluorescence was observed for test material treated with everything but labeled trypsin, or when the control material (devoid of clay) was exposed to fluorescently labeled trypsin and processed as the test material was (data not shown).

The foregoing description of embodiments of the invention has been presented for purposes of illustration and description. It is not intended to be exhaustive or to limit the invention to the precise form disclosed. Obvious modifications or variations are possible in light of the above teachings. The embodiments were chosen and described to provide an illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. A method of sequestering skin irritants present on the surface of the skin comprising the step of applying to the skin a combination consisting essentially of a personal care article selected from the group consisting of diapers, training pants, adult incontinence products, underpants, feminine care products, and bath tissue paper; an unmodified particulate skin irritant sequestering agent that can sequester a fecal enzyme, the unmodified particulate skin irritant sequestering agent being selected from the group consisting of clay, silica, titanium dioxide, hydroxyapatite, alumina, refractory metal oxide, ion-exchange resin, and any combination thereof; and a lipophilic skin health benefit agent having an average hydrocarbon chain length greater than C-8.

2. The method of claim 1, wherein the absorbent article has a body facing region and the unmodified particulate sequestering agent and the lipophilic skin health benefit agent are disposed on the body facing region.

3. The method of claim 1, wherein the fecal enzyme is trypsin.

4. The method of claim 1, wherein the unmodified clay comprises bentonite.

5. The method of claim 1, wherein the unmodified clay comprises laponite.

6. The method of claim 1, wherein the unmodified clay is selected from the group consisting of montmorillonite, beidelite, hectorite, saponite, stevensite, and any combination thereof.

7. The method of claim 1, wherein the lipophilic skin health benefit agent is selected from stearic acid, isoparaffin, petrolatum, and any combination thereof.

8. The method of claim 1, wherein the lipophilic skin health benefit agent is selected from fatty acid, fatty acid esters, fatty alcohol, triglyceride, phospholipid, mineral oil, essential oil, sterol, sterol ester, emollients, waxes, and any combination thereof.

9. The method of claim 1, wherein the unmodified particulate skin irritant sequestering agent and the lipophilic skin health benefit agent are contained within a lotion vehicle.

10. The method of claim 9, wherein the lotion vehicle comprises from about 0.1 to 25 weight percent of the unmodified particulate skin irritant sequestering agent and from about 5 to 95 weight percent of the lipophilic skin health benefit agent, based on the total weight of the vehicle.

11. The method of claim 10, wherein the lotion vehicle further comprises from about 0.1 to 25 weight percent of a polymeric viscosity enhancer, based on the total weight of the vehicle.

12. The method of claim 1, wherein the unmodified particulate skin irritant sequestering agent is present in a concentration such that when applied to the skin at least 50 ug/cm$^2$ is transferred to the skin.

13. The method of claim 1, wherein the skin irritant is bound to the sequestering agent on the absorbent article.

14. The method of claim 1, wherein the skin irritant is bound to the sequestering agent on an individual's skin.

* * * * *